(12) United States Patent
Amberg-Schwab et al.

(10) Patent No.: US 11,555,123 B2
(45) Date of Patent: Jan. 17, 2023

(54) EDIBLE FUNCTIONAL COATINGS AND HYBRID POLYMER-BASED COATINGS FOR PHARMACY AND FOOD

(71) Applicant: FRAUNHOFER-GESELLSCHAFT ZUR FOERDERUNG DER ANGEWANDTEN FORSCHUNG E.V., Munich (DE)

(72) Inventors: Sabine Amberg-Schwab, Erlabrunn (DE); Daniela Collin, Werneck (DE); Anika Deinhardt, Waigolshausen (DE)

(73) Assignee: Fraunhofer Gesellschaft zur Foerderung der angewandten Forschung e.V., Munich (DE)

( * ) Notice: Subject to any disclaimer, the term of this patent is extended or adjusted under 35 U.S.C. 154(b) by 131 days.

(21) Appl. No.: 17/201,103

(22) Filed: Mar. 15, 2021

(65) Prior Publication Data
US 2021/0198495 A1 Jul. 1, 2021

Related U.S. Application Data

(62) Division of application No. 16/095,763, filed as application No. PCT/EP2017/059873 on Apr. 26, 2017, now abandoned.

(30) Foreign Application Priority Data

Apr. 26, 2016 (DE) .................... 102016107760.7

(51) Int. Cl.
*C09D 1/04* (2006.01)
*A23P 20/10* (2016.01)
(Continued)

(52) U.S. Cl.
CPC .............. *C09D 1/04* (2013.01); *A23P 20/105* (2016.08); *A61K 9/282* (2013.01); *A61K 47/24* (2013.01); *C09D 7/60* (2018.01)

(58) Field of Classification Search
CPC ... C09D 1/00; C09D 7/60; C09D 1/04; C09D 7/40; A23P 20/10; A23P 20/105; A61K 9/282; A61K 47/34; A61K 47/24
See application file for complete search history.

(56) References Cited

U.S. PATENT DOCUMENTS 3,471,304 A 10/1969 Mokhtar et al.
4,661,359 A 4/1987 Seaborne et al.
(Continued)

FOREIGN PATENT DOCUMENTS

DE 19613650 C1 4/1997
DE 19615192 A1 10/1997
(Continued)

OTHER PUBLICATIONS

Kricheldorf et al., "Telechelic and Star-Shaped Poly($\varepsilon$-caprolactone) Functionalized with Triethoxysilyl Groups—New Biodegradable Coatings and Adhesives", Macromolecular Chemistry and Physics, vol. 206, Issue 7, Apr. 8, 2005. (Year: 2005).*
(Continued)

*Primary Examiner* — Jianfeng Song
(74) *Attorney, Agent, or Firm* — Laurence A. Greenberg; Werner H. Stemer; Ralph E. Locher (57) ABSTRACT

A composition contains silicic acid polycondensate modified with organic groups, as a coating for medicines and foodstuffs or as a component in such a coating. The organic groups are partially or wholly biodegradeable. A method for producing a product coated with the composition and a coated product are further described.

4 Claims, 1 Drawing Sheet

(51) Int. Cl.
  *C09D 7/60* (2018.01)
  *A61K 9/28* (2006.01)
  *A61K 47/24* (2006.01)

(56) References Cited

U.S. PATENT DOCUMENTS

| | | | |
|---|---|---|---|
| 4,710,228 | A | 12/1987 | Seaborne et al. |
| 5,741,505 | A | 4/1998 | Beyer et al. |
| 5,973,176 | A | 10/1999 | Roscher et al. |
| 6,979,463 | B2 | 12/2005 | Kou |
| 2007/0141104 | A1* | 6/2007 | Hauenstein ............ A61L 31/16 427/2.24 |
| 2010/0062116 | A1 | 3/2010 | Noort et al. |
| 2015/0250731 | A1 | 9/2015 | Hoppu et al. |

FOREIGN PATENT DOCUMENTS

| | | |
|---|---|---|
| EP | 0802218 A2 | 10/1997 |
| EP | 1112738 A2 | 7/2001 |
| EP | 0839008 B1 | 9/2001 |
| WO | 03007736 A1 | 1/2003 |
| WO | 2007076288 A2 | 7/2007 |
| WO | 2012116814 A1 | 9/2012 |
| WO | 2013087757 A1 | 6/2013 |
| WO | 2015031663 A1 | 3/2015 |

OTHER PUBLICATIONS

Shen, Elizabeth: "Cover Up." Innovations in Pharm Tech 52 (2015): 44-47].

Abbaspour, Mr: "Study of Free-Films and Coated Tablets Based on HPMC and Microcrystalline Cellulose, Aimed for Improve Stability of Moisture-Sensitive Drugs"; Jundishapur Journal of Natural Pharmaceutical Products 2010; 5(1): 6-17.

Unalan, I, et al. "Nanocomposite films and coatings using inorganic nanobuilding blocks (NBB): current applications and future opportunities in the food packaging sector"; RSC Adv., 2014, 4, 29393.

Rudnik, E.: "Compostable Polymer Materials". Amsterdam: Elsevier, 2008.

Liu, P. et al.: "Microstructure and Thermal Properties of Silyl-Terminated Polycaprolactone—Polysiloxane Modified Epoxy Resin Composites". Journal of Applied Polymer Science 109 (2008), S. 1105-1113).

Dong, S, et al.: "Fluorescently Labeled Cellulose Nanocrystals for Bioimaging Applications". J. AM. Chem. Soc. 2007, 129,13810-13811.

Amberg-Schwab, S.: "Functional Barrier Coatings on the Basis of Hybrid Polymers". Handbook of Sol-Gel Science and Technology, vol. 3, Ed.: S. Sakka.

Amberg-Schwab, S., et al.: "Wenn die Verpackung bio wird!". Farbe und Lack, Bd. 121, 2015,H. 10, S. 60-6.

* cited by examiner

EDIBLE FUNCTIONAL COATINGS AND HYBRID POLYMER-BASED COATINGS FOR PHARMACY AND FOOD

CROSS-REFERENCE TO RELATED APPLICATION

This is a divisional application of U.S. patent application Ser. No. 16/095,763, filed Oct. 23, 2018, which was a national stage application, under 35 U.S.C. § 371, of International Patent Application PCT/EP2017/059873, filed Apr. 26, 2017, which designated the United States; this application also claims the priority, under 35 U.S.C. § 119, of German patent application No. DE 10 2016 107 760.7, filed Apr. 26, 2016; the prior applications are herewith incorporated by reference in their entirety.

BACKGROUND OF THE INVENTION

Field of the Invention

The present invention relates to the use of a composition containing silicic acid (hetero) polycondensate modified with organic groups, as coating of medicines and food. In addition, the present invention relates to a method for producing a coating product and a coating product.

1. Drugs

In order to pack medicines, e. g. PVDC (polyvinylidene chloride) and aluminum composite films have been used so that the active ingredients can be sufficiently protected from moisture, oxygen, UV radiation and mechanical damage.

To avoid the use of chlorine-containing films and aluminum packaging for the packaging of pharmaceuticals, one has been looking for alternative materials that often have to be deep-drawable with consistently good barrier properties.

In order to meet the very high demands on the barrier of pharmaceutical packaging, mostly PVDC or PVC are used as a composite foil. The water permeability of a composite foil is, for flat films, usually between 0.09 $g/m^2 \times d$ (e. g. for 51 µm PCTFE (polychlorotrifluoro ethylene) on PVC and 4 $g/m^2 \times d$ (e. g. for 250 µm thick PVC). After thermoforming, it increases to about 2.5-3.5 times.

In addition to the barrier properties of the packaging, medicines or tablets also coated themselves. In addition to additional barrier effect, these coatings meet further tasks (see below). However, the barrier effect of tablet coating alone not sufficiently effective.

Coatings for tablets and medicines generally have very different functions. They serve e. g.:
- the protection of the active ingredients against light, atmospheric oxygen and moisture and thus prevent aging
- mechanical stabilization during manufacture, packaging and shipping
- the protection of the active substance against the influence of digestive juices (pH-dependent solubility)
- the controlled release in the human body; solubility adapted to the intended use
- avoiding side effects of the active substance
- the identification of different drugs by differentiating the tablets
- improving the swallowing properties
- if the drug is to be taken as a suspension (dissolved mostly in water), good solubility or dispersibility is important
- possibility to form an aesthetic/beautiful surface
- odor, taste and colorlessness and health safety
- compatibility with the excipients and active ingredients in the core
- compatibility with common film additives such as plasticizers, dyes and fillers
- no filling of the engraving.

The selection of the polymer film used for the coating of pharmaceuticals depends, inter alia, on where and in what time span the active substance is to be released. If a fast release (fast release) is desired, the nuclei can be coated with polymers soluble in gastric juice that dissolve in a pH environment of 1-3.5. On the other hand, sustained-release or gastric acid-sensitive drugs are coated with polymer layers that dissolve or swell at a pH of 6.5-8.0 to allow the drug to diffuse through the swollen film.

None of the polymers known to date meets all the desired criteria for coating materials at the same time. Therefore, the polymers are often selected for each of the three main applications of the drug in question, and other excipients are used to make appropriate combinations of properties. The following discusses the state of the art solutions for first enteric coatings and non-resistant coatings, followed by coatings for a controlled release and aesthetic coatings.

Dragées, tablets, capsules, pellets and granules coated with enteric coatings have long played a major role in the group of solid oral dosage forms. Common film coatings are based, for example, on methyl cellulose or other cellulose derivatives with different gastric juice solubilities.

In order to be able to control the release of the active ingredients enclosed in the drug core over a defined period of time, cellulose derivatives are also used. These coatings allow controlled drug release by controlled degradation.

In process for aesthetic coating, almost exclusively polymers are used which are good and fast water-soluble. About 60-70% of the coatings contain hydroxypropyl methylcellulose (HPMC).

It has been shown that with state-of-the-art tablet coatings, in addition to the already discussed properties, such as enteric resistance, controlled drug release or aesthetics, the water vapor barrier can already be improved [Shen, Elizabeth. "Cover Up." Innovations in Pharm Tech 52 (2015): 44-47]. However, this is far from sufficient to be able to save on the packaging material in the future, as discussed above.

Modified PVA has a very good initial water vapor barrier. The material nevertheless has a water absorption capacity, whereby the coating swells and loses barrier when it is exposed to a moist environment for a long time. However, this means that the high-quality packaging material with excellent barrier effect cannot be saved.

In addition to the previously described coating solutions already in use, there are numerous papers in the patent and technical literature for the optimization of the barrier properties by coating the tablets with new materials or material concepts. These are summarized below.

EP 0 839 008 B1 describes an edible inorganic coating on foods and pharmaceutical products, as well as the production of these. This inorganic coating (constituents: $SiO_2$, SiO, CaO, ZnO, $TiO_2$, MnO) serves as a barrier layer against water vapor and oxygen. It is said to improve storage stability but not affect the taste and texture of the actual product. Disadvantages of this vacuum deposited coating, on the one hand, are that it has to be very thin (ideally between 0.0005-0.02 µm) in order to avoid cracking or flaking off and, on the other hand, the coating process by sputtering or CPD is very expensive, complex and time consuming.

U.S. Pat. No. 3,471,304 A, 4,661,359 A and 4,710,228 A disclose edible moisture barrier coatings of shellac and also cellulose ethers, monoglycerol, metal salts and fatty acids as coating agents for food products and as enteric-coated coating compositions for sustained release or for release in the intestine. These do not meet the necessary barrier requirements for the pharmaceutical industry.

In many patents (e. g. WO 2015/031663 A1), lipids, fats, oils and fatty acids are disclosed as moisture barrier additives. These already have a natural hydrophobic effect. However, the barrier effect is far from being comparable with the ORMOCER® barrier coatings and is therefore not sufficient on its own. The specified water absorption is, for example, max. 1% if stored at 40° C. and 75% relative moisture for 30 min.

Abbaspour M R, Sharif Makhmalzadeh B, Jalali S; Jundishapur Journal of Natural Pharmaceutical Products 2010; 5 (1): 6-17 discloses that moisture barrier layers should have low permeability to water vapor but should also dissolve quickly in the body and therefore must be readily water soluble. So far no material is known which satisfies both aspects, therefore the industrial approach is usually a compromise between a good water vapor barrier and a good solubility in water. This is mostly achieved by water-soluble polymer films as film formers and the incorporation of particles with hydrophobic or scavenger properties.

For instance, this can be stearic acid (obtained by saponification from vegetable and animal oils and fats), or act as a moisture scavenger, such as microcrystalline cellulose, which acts like a molecular sponge in contact with water. The disadvantages of this development is, first, that the incorporation of microcrystalline cellulose the coating becomes opaque or white, respectively. In addition, the layer thickness with 100-200 µm is very uninteresting from the economic point of view. The water vapor barrier improved only slightly.

Unalan I U, Cerri G, Marcuzzo E, Cozzolinoa C A, Farris S; RSC Adv., 2014, 4, 29393 discloses that the embedding of nanoparticles in the coating increases the diffusion path and thereby improves the barrier effect. For pharmaceutical products and food, however, the use of nanoparticles should be viewed critically and should be excluded if possible, since diffusion of these particles into cells is not completely ruled out. Literature describes this concept for the packaging as such.

WO 12/16814 describes the deposition of inorganic layers, such as metal oxides, on pharmaceutical products by means of ALD (atomic layer deposition). However, this process is not only very expensive and laborious (vacuum process), but homogeneous layers on 3D objects are difficult to generate, especially when it comes to mass production. Pure inorganic coatings are also very brittle and prone to cracking and flaking off.

US 2015/0250731 A1 describes a method for tablet coating and for a pharmaceutical formulation. The coating is applied to the pharmaceutical substrates by means of ALD (atomic layer deposition). A similar method—MLD (molecular layer deposition) is suitable according to the patent for the deposition of hybrid organic-inorganic layers, which are combined in advance by simple mixing. Inorganic oxides are used as precursors. Biomaterials such as hydroxyapatite, polymers, sugars, nanolaminates and the like may also be deposited thereover. Here, the desired precursors are simply mixed in the desired ratio.

In summary, the above consideration of the prior art shows that the known tablet coatings by no means meet the high requirement profile with regard to the barrier effect. There is therefore a great need for improved barrier coatings.

2. Foods

For food, there are different coating concepts compared to medicines, as the requirements are often very diverse and specific. In general, however, there is also the need and desire to improve the shelf life of the products by means of suitable barrier layers. For example, oxygen entering through the barrier layer leads to oxidation of fats ("rancidity"), to vitamin depletion and to flavor destruction. The entry of water vapor can lead to loss of crispiness, clumping of hygroscopic products and growth of microorganisms.

In contrast to tablet coatings, the visual appearance is particularly important in foods. Ideally, the customer should not be aware that the product has been optimized by the chemical route. Therefore, in this case, functional coatings with high barrier effect and other functionalization and customization options are an advantage.

For food applications, the coatings can be applied to the food by various methods, such as by dipping, spraying, brushing and panning, followed by a drying process.

Edible coatings have been divided into four categories: polysaccharides, lipids, proteins and composites.

Composites are edible films and coatings and often consist of a mixture of polysaccharides, proteins and/or lipids. WO 2013/087757 A1 discloses an edible coating wherein the first layer consists of an edible oil and a second layer of hydrophobic edible particles (diameter 20 nm-500 µm). The particles consist of either an inorganic core material and a hydrophobic shell (fats, oils, etc.) or entirely one hydrophobic material such as wax. Applications are for potato chips, biscuits, cornflakes, fruits, ice cream waffles etc. As a result, cornflakes, for example, do not absorb milk so quickly and still have a very good crunch.

U.S. Pat. No. 5,741,505 A discloses an inorganic coating on foods and pharmaceutical products as a moisture/gas barrier. These inorganic coating materials include $SiO_2$, SiO, MgO, CaO, TiO2, ZnO and MnO. To prevent cracking, the coating should be thinner than 0.05 µm. These thin layers improve the haptics problem, which has sometimes resulted from thick organic coatings. Cornflakes that do not soak up in milk so fast are mentioned as a possible application.

WO 2003/007736 A1 discloses a continuous fat layer with 1-15% water-insoluble and fat-insoluble particles (diameter 0.05-100 µm). These particles are inorganic components $SiO_2$, silicates, talcum, clay materials and phosphates. In addition, organic materials such as microcrystalline cellulose and insoluble cellulose derivatives can be used.

U.S. Pat. No. 2,010,062 116 discloses a coating of microwaveable foods for crispy appearance. Incorporation of a susceptor in the coating, which converts the microwave radiation into heat. Hereby, the mechanism of microwave heating is transformed into one that is comparable to a conventional oven heating process. The composition of the coating contains at least one prolamine and at least one hydrocolloid or gelling agent.

Enteric coated coated dragées, tablets, capsules, pellets and granules have long played a major role in the group of solid oral dosage forms. Enteric resistance is achieved today by coating the dosage form with acidic polymers which are protonated in the stomach and are insoluble in this form. The acidic groups only dissociate in the neutral to weakly basic environment of the thin or large intestine, thereby converting the polymer into its ionic and therefore soluble form. Enteric coatings serve to protect the stomach lining from aggressive drugs, to prevent the premature inactivation of acid-labile drugs, to release drugs targeted in the small or large intestine or to cover unpleasant taste and odor properties of drugs. Coatings on foods can prevent the release of odors from them and, moreover, protect the food from moisture and undesirable oxidation reactions causing oxygen.

BRIEF SUMMARY OF THE INVENTION

In view of the prior art described above, the problem to be solved is to achieve excellent barrier values, which are necessary for the protection of medicines or food, while eliminating the need for chlorine-containing or aluminum-containing packaging and coatings and to be able to dispense with other expensive or questionable procedures.

Another object is to provide moisture barrier layers that have a good balance between a low permeability to water vapor and rapid dissolubility in the body and therefore have good water solubility.

A further object of the present invention is to prepare medicaments and foods such that the packaging materials which can be used for them do not necessarily have to have particularly good barrier properties, while the medicaments or foods are still sufficiently protected against moisture and gases such as oxidizing oxygen. Because packaging materials are often subjected to a deep-drawing process. However, deep-drawn packaging materials have less good barrier properties than non-thermoformed ones.

Another object of the present invention is to provide a material for the food and pharmaceutical industry which is a functional coating. The material or the layer composite can be biodegradable and develop an antimicrobial effect only on contact with moisture, this coating preferably having good barrier properties against the passage of oxygen and water vapor, in order to protect the contents e. g. from oxidative processes.

The above object is achieved in that the advantageous and desired properties are already realized in a coating of the drug or the food.

The present invention provides the use of a composition containing silicic acid (hetero) polycondensate modified with organic groups as a coating of a substrated selected from a drug and food or as a component of such a coating, wherein the organic groups of the silicic acid (hetero) polycondensate are at least partially biodegradable.

The present invention also provides a method for producing a coating product comprising the following steps:
  (i) applying a composition which is optionally present in a diluent and/or solvent and contains silicic acid (hetero) polycondensate modified with organic groups, on a substrated selected from a drug and food;
  (ii) drying and/or curing the composition.

The composition used in the preparation of the coating product is preferably the composition used in connection with the use according to the invention.

The present invention also provides a coating product obtained by the above-mentioned method and a coating product comprising a substrate selected from a drug and food and a coating applied to the substrate, the coating having a composition containing silicic acid (hetero) polycondensate modified with organic groups.

The term "substrate" as used herein is not particularly limited and means any drug or food that can be coated. The prerequisite for the coatability is a solid state or a state in which at least one defined and stable surface is present. As used herein, the term "pharmaceutical" or "drug" refers to any pharmaceutical or drug for humans and animals that meets the stated substrate requirements. Here, a drug includes both prescription drugs and over-the-counter remedies, such as cough drops. The inclusion in the human or animal body includes not only the oral inclusion and subsequent swallowing, but also the inclusion via the nose or other body orifices and the intake into the mouth and the subsequent sucking or dissolving in the mouth or chewing without swallowing. The inclusion of another body opening is, for example, the rectal uptake of suppositories. Typical examples of drugs are solid peroral dosage forms such as enteric coated coated tablets, tablets, capsules, pellets and granules.

As used herein, the term "food" refers to any food or food for humans or animals or other means of incorporation into the human or animal body which meets the stated substrate requirements. Another means is, for example, a dietary supplement or other supplements, such as vitamins or minerals. Intake into the human or animal body involves not only oral ingestion and subsequent swallowing, but also ingestion into the mouth and subsequent suckling or chewing without swallowing.

As used herein, the terms "coating" or "covering" or "to coat" or "to cover" refer to the application of a substance to the surface of a substrate, wherein the surface of the substrate may be completely or partially covered. The thickness of the coating or covering is not limited and varies depending on the size of the substrate, the nature of the surface of the substrate, and the use of the coating. A typical range of thickness is 1 µm to 1 mm. As mentioned, the coating materials of the invention are biodegradable; they behave safely in the body and are easily metabolized. With the materials according to the invention it is therefore possible to provide layers in the field of tablet coatings or food coatings for the first time.

At the same time, desired properties of the layers, e. g. barrier properties, can be set. This is accomplished, inter alia, by a combination of one or more layers of the inventive material with one or more very thin, purely inorganic layers that are e. g. sputtered.

The solubility of the layers in the stomach or in the small intestine can also be adjusted. The Si—O—Si bonds of the condensates according to the invention are usually acid stable, but base labile, so that the product coated therewith, when the coating is complete, passes through the stomach undigested, but is degraded in the small intestine. This is important for a number of tablet applications. However, such condensates can also be modified to be acid labile. This is achieved by the modification with suitable groups bonded to silicon via carbon, as is known to the person skilled in the art. The acid lability can also be adjusted by a reduction of the degree of crosslinking, especially of the degree of inorganic crosslinking (i. e. the Si—O—Si or Si—O-metal bonds).

The coating materials according to the invention can be applied as lacquers. They are particularly favorable because they can achieve barrier properties with respect to water vapor and oxygen.

For the biodegradability of the coating, it is necessary that the largest possible proportion of the organic groups integrated into the inorganic network of the hybrid material is biodegradable. After incorporation of the product into the body, the coating can be converted by metabolic processes into natural metabolic products, such as $CO_2$ or $H_2O$. Also, degradation products can be introduced into human metabolism. The only remains are essentially only the inorganic constituents of the previous hybrid material (e.g. $SiO_2$), which already occur in nature in the form of natural minerals and excreted by the organism.

With the help of the coating applicable according to the invention, excellent barrier values for water vapor and oxygen can be achieved, which are necessary to protect the pharmaceutical products, in particular tablets, drug and the like, or food. The protection of pharmaceutical products and food can thus be partially or completely realized by such a coating, which makes an often chlorine-containing or aluminum-containing packaging superfluous or allows a waiver of other expensive or questionable procedures.

The coating according to the invention is produced by applying a corresponding coating varnish to the desired pharmaceutical, in particular a tablet, or the desired foodstuff. If it contains solvents, it can be removed if necessary. Alternatively or cumulatively, a thermal aftertreatment or an irradiation with light is possible.

The inorganic component of the coating lacquer according to the invention consists of silicon cations, optionally in combination with other cations such as aluminum, zirconium, titanium or boron, and combinations thereof, which are linked together via oxygen bridges and thereby form a network. This is an organically modified silicic acid or, in the case of the presence of other metal ions, an organically modified silicic acid hetero-polycondensate. An example of such a heteropolycondensate is a condensate containing silicon and aluminum and optionally further cations. In the following, the term silicic acid (hetero) polycondensate is used as a common term for the pure silicic acid polycondensates and heteroatoms-containing polycondensates.

The organically modified silicic acid (hetero) polycondensate is usually produced by hydrolytic condensation of silanes, optionally in combination with co-condensable compounds of other metal ions. These silanes may carry carbon-bonded organic groups in addition to hydrolyzable groups such as alkoxides or hydroxide groups. These groups remain attached to the respective silicon atoms in the hydrolytic condensation, and the polycondensate is suitably modified with them.

For this reason, the biodegradable organic groups are preferably present in the condensate at least partially via Si—C bonds. However, this does not exclude the possibility of using polycondensates with oxygen-bonded biodegradable organic groups. Such polycondensates are known to the person skilled in the art.

Biodegradable groups are integrated in the silicic acid (hetero) polycondensate of the present invention as mentioned organic. With respect to these groups, those skilled in the art can refer to materials known in the art. Various types of substances, including oligo- and polymers, which can be used in the present invention, are mentioned below.

Many polymers are known in the prior art which are readily and rapidly soluble in water. Often they are saccharide derivatives. Examples are hydroxypropylmethylcelluloses (HPMC), methylcelluloses (MC), sodium carboxymethylcellulose (NaCMC), hydroxyethylcellulose (HEC), hydroxypropylcellulose (HPC), polyvinylpyrrolidone (PVP) and polyvinyl alcohol (PVA). HPMC forms highly water soluble films that tend to be brittle. MC is a water-soluble polymer. However, the high viscosity of the solution makes processing difficult. A tendency to retardation was also observed. NaCMC is a widely used and highly water-soluble polymer with a strong thickening effect. A significant disadvantage is the partially insufficient mechanical properties of the films of NaCMC. HEC is rarely used as a film coating because of its high tack but is more commonly used as a primer. HPC is an extremely tacky polymer that forms mechanically stable films. HPC alone is hardly used, but much better to process as co-polymer. PVP alone forms a sticky solution and a brittle film, but increases gloss and color homogeneity with HPMC. PVA as a polymer alone is very sticky. It improves the mechanical properties as a co-polymer (Kollicoat/BASF).

Polysaccharides, which can be used as the modifying organic groups in the present invention and are already used in the art for edible coatings or coatings include cellulose, starch derivatives, pectin derivatives, seaweed extracts, gum arabic and chitosan. Polysaccharides are usually very hydrophilic and have poor water vapor and gas barrier properties. They are mainly used as sacrificial layers for food products.

Cellulose and derivatives thereof provide good film-forming properties which are odorless, tasteless, flexible and transparent. They have a moderate strength and are resistant to oils and fats, but have poor water vapor barrier properties.

Chitosan can form partially permeable coatings so that the internal atmosphere can be modified. This delays the ripening and degradation process in fruits and vegetables. Coatings made of chitosan are transparent, robust, flexible and have good oxygen barrier properties. $CO_2$ permeability could be improved by methylation of the polymers. They are biodegradable, biocompatible and chemically inert and also relatively cheap.

Starch is used in industrially produced foods because it is biodegradable and edible, is abundant, low in cost, non-allergenic, and easy to process. Coatings with high amylose content have a good oxygen barrier, are flexible, resistant to oil. They are odorless, tasteless, transparent, bioabsorbable, semipermeable for $CO_2$.

Carrageenan involves a gelling mechanism which forms a 3-dimensional network of polysaccharide double helixes in a moderate drying process. This solid film is used for desserts, ice cream, milkshakes, salad dressings, condensed milk and sauces to increase the viscosity. It is also used in beer, toothpaste, soy milk and many other products.

Other materials may be suitable. Acetylated glycerol monostearates can be stretched to 800% of their original length. The moisture barrier is significantly worse than the polysaccharides. They are used for poultry and meat products to the minimize fluid loss during storage.

The abovementioned materials can be used as such to be bound to suitable silanes or already hydrolytically condensed silicic acid homo- and/or heteropolycondensates and thus to incorporate biodegradable groups into the condensate. Alternatively, ingredients thereof or degradation products thereof, such as individual sugar components, may be used therefor. To be able to be connected, the materials or groups preferably require at least one free OH or carboxylic acid group, which can be bound e.g. via a silicon-bonded, isocyanate- or epoxy-containing group, as explained in more detail below.

It is also possible to use composites. Edible films and coatings consist of a mixture of polysaccharides, proteins and/or lipids. The goal is to produce such composite films that have improved barrier or mechanical properties depending on the application.

These are preferably one or more types of organic monomers, oligomers or polymers, such as caprolactone/caprolactam polymers, for example polycaprolactone, polycaprolactone triol or derivatives of polycaprolactone triol, polylactic acid, biobased waxes such as cutins, chitosan or hemicelluloses or celluloses, including cellulose derivatives and/or cellulose building blocks. The term "cellulose building blocks" is intended to mean all monomers, oligomers and polymers which have at least two β-D-glucose units having a β-1,4-glycosidic bond and at least one OH group. Favorable are groups are those whose hydrocarbon chains are interrupted by one or more ester and/or amide and/or ether and/or urethane groups such that only a few carbon atoms directly follow one another.

Particularly preferred are one or more types of organic polymers, both bio-based biodegradable natural products and natural product derivatives such as chitosan, cellulose, cellulose derivatives and/or cellulose building blocks, as well as petroleum-based biodegradable starting materials, e.g. polycaprolactone triol (PCL-T).

An example of a biodegradable plastic is petrobased polycaprolactone (PCL). The polyester is prepared from the cyclic ε-caprolactone by a ring-opening polymerization reaction. The thermoplastic has a low glass transition temperature of −60° C., giving it a waxy consistency. The good water, oil and solvent resistance makes PCL suitable for applications of all kinds, such as for packaging or as a carrier material for cells in tissue engineering interesting. PCL can be biodegraded by the enzyme lipase. The optimum degradation temperature of PCL is 50° C. (RUDNIK, E.: Compostable Polymer Materials. Amsterdam: Elsevier, 2008). The polymer chains of the PCL contain a maximum of 5 carbon atoms, each located between a carboxy group and an ether group (or a terminal OH group), and thus fall within the above definition of groups having carbon chains that are interrupted by one or more ester and/or amide and/or ether and/or urethane group(s). In the hydrolysis of PCL, the molecule is cleaved to give 6-hydroxycaproic acid, which is completely metabolized in the citric acid cycle.

Preferably, at least a portion of the organic, biodegradable groups of the coating material which can be used according to the invention is bound to a silicon atom via a carbon atom in each case. Since the underlying organic molecules usually have free hydroxyl and/or carboxylic acid groups, the connection is formed in a simple manner e.g. by reaction with silanes bearing a silicon-bonded group substituted with an isocyanate group. Isocyanate groups can react both hydroxy groups (to form a urethane group) and with carboxylic acid groups (to form an amide group and free $CO_2$). Examples of suitable isocyanate silanes are alkoxysilanes of the formula $R_aSiX_{4-a}$, where X is a hydrolysis-sensitive group or a hydroxy group, in particular an alkoxy group, more preferably methoxy or ethoxy. R represents an isocyanatoalkyl group, and a is 1 or 2, with 1 being preferred. The isocyanatoalkyl group may be the isocyanatopropyl group. For example, the common isocyanatopropyltriethoxysilane is a suitable silane for the purposes of the invention. Of course, instead of the isocyanato group, those skilled in the art will be familiar with other groups which, usually by condensation reactions, react with carboxylic acid or hydroxy groups, such as amino or optionally activated carboxylic acid groups. Silanes containing such groups bonded to silicon via carbon are known in large numbers and are equally suitable for binding the said organic molecules.

In a preferred embodiment, silanes having caprolactone derivatives are produced via the coupling reaction with the isocyanate group.

In a likewise preferred embodiment which can be combined with all other embodiments of the invention, an organic, biodegradable group containing at least two short carbon chains in a branched position as defined above is selected. Polycaprolacton-triol (PCL-T) proved to be particularly suitable for this embodiment. It is a PCL derivative based on three PCL chains linked by a 1,1,1-trimethylolpropane moiety:

The liquid that is highly viscous at room temperature (molecular mass about 300 g/mol) is biodegradable. All existing hydroxy groups of the PCL-T are equally reactive with respect to the reaction partner used, i. e. the isocyanate silane. The number of silanes that can be attached to one molecule of PLC-T is therefore controlled by stoichiometry. According to the invention, the functionalization of one or two hydroxy groups has proved favorable. Depending on the choice of the index a in the compound $R_aSiX_{4-a}$, the result is a mono- or disilane, wherein the silane atoms carry two or three hydrolysis-sensitive groups. In the following formula scheme, a triethoxysilane was used, that is, a silane of the formula $R_aSiX_{4-a}$, where R is ethoxy and a is 1. However, it should be clear that R and a can also have different meanings as explained above.

Each of the hydroxy groups of the PLC-T can be linked with a silyl radical via a Si—C bond, for example via the above-mentioned isocyanate coupling. The reaction scheme for preparing the silyl-functionalized PLC-T can be represented as follows:

-continued

R =

The silyl group-functionalized PLC-T is hereinafter referred to as PCL-T-1/3-triethoxysilane, and the two silyl groups-functionalized PLC-Twill be referred to as PCL-T-2/3-triethoxysilane.

Alternatively, for example cellulose can be incorporate into the inorganic network instead of PLC-T. In these cases, cellulose was functionalized with epichlorohydrin to give epoxy- or diol-functionalized cellulose. Cellulose can be integrated in the silicic acid (hetero) polycondensate through a crosslinking reaction with an epoxy group-containing silicic acid (hetero) polycondensate.

The two reaction variants show two of the many possibilities of incorporation of the biodegradable groups: In the former case, these groups are linked via an Si—C bond, in the latter case via a connection to the organic network.

In order to control the relation of the inorganic network to the organic moiety, the hydrolytic condensation of the silanes modified with organic, biodegradable substituents as described above can be carried out in the presence of further hydrolytically condensable compounds of the formula $M^b(X)_b$ where M is selected from a metal which can be incorporated, as described above, via oxygen atoms in the inorganic network of the silicic acid (hetero) polycondensate. For instance, the metal is selected from Al, Si, Zr, Ti, B, while b represents the formal oxidation state of this metal and X means, as described for the silanes, a hydrolysis-sensitive group or a hydroxy group. For example, a tetraalkyl orthosilicate of the formula $Si(OR)_4$ with R=methyl or ethyl and/or an aluminum alcoholate can be used as compound of the formula $M^b(X)_b$. The latter may be complexed to slow the hydrolytic condensation reaction of this component in sol-gel formation, resulting in the formation of broader network structures.

Furthermore, it is preferred that the coating lacquer which can be used according to the invention has good coating properties. For this purpose, it is advantageous, although not mandatory, to add one or more components which positively influence the coating (film formation) and/or barrier properties. These can be, for example, organic components or components with an organic content that can be organically polymerized and thus form an additional organic network to increase the barrier effect of the coating, and/or have polar groups to improve the adhesion to the substrate. Suitable organically polymerizable groups are groups having reactive rings such as epoxy groups or having non-aromatic C=C double bonds such as (meth)acrylic groups, in particular (meth)acrylate groups. Thermal organic polymerization is superior to organic polymerisation by light, because thermal curing is technically very easy to realize. Optionally, however, this may be unfavorable, for example when the substrate is sensitive to heat, which is why light-induced polymerizable groups may be suitable. The presence of epoxy groups is particularly preferred not only because they can be subjected to heat-induced polymerization, but also because hydroxy groups are formed during polymerization, which ensure good adhesion to the substrate.

The component which positively influences the coating properties is preferably an inorganic component having an organic portion, namely a silane having a carbon-bonded radical bearing an organically polymerizable group, for example, an epoxy silane or a (meth)acrylic silane. An alkoxy-modified epoxysilane, e. g. of (3-glycidyloxypropyl)trimethoxysilane, known by the abbreviation GLYMO, can be suitably use. This silane, together with the silane carrying the biodegradable component and optionally one or more hydrolytically condensable compounds of the formula $M^b(X)_b$, may be subjected to a hydrolytic condensation reaction.

In addition, it is desirable that the layers obtained by application of the lacquer have good barrier properties with respect to the passage of oxygen and water vapor. Experience has shown that good barrier effects to oxygen and water vapor are accompanied by barrier effects, as compared to other gases, vapors and odors. This is e. g. very important if the tablets to be coated are to be protected from such gases, vapors or odors, or to prevent the release of odors or to reduce odors that come from food to be coated.

The coating material suitable for coating food or tablets according to the invention can be prepared as follows:
(a) Sol-gel production of a silicic acid (hetero) polycondensate by hydrolytic condensation of
(i) at least one tetraalkyl orthosilicate and/or at least one glycidyltrialkoxysilane, as well
(ii) a polycaprolactone derivative functionalized with one or two silyl groups, preferably a polycaprolactone triol having at least two components $[O—(CH_2)_m—C(O)—O]_n$, where m is an integer between 2 and 8 and n is 1, 2 or 3 or greater than 3, where n can assume different values, wherein the silicic acid (hetero) polycondensate is furthermore produced
(iii) optionally using a hydrolytically condensable aluminum compound, preferably a complexed aluminum tert-butylate, as well as
(iv) a solvent selected from alcohols and acetylacetonate group-containing compounds, optionally in admixture with water, and optionally
(b) incorporating an antibacterial agent in the silicic acid (hetero) polycondensate.

In particularly favorable embodiments of the invention, the inventive coating material is used in combination with an inorganic layer, preferably deposited from the gas phase, such as SiOx with x=1.5-1.8, or another metal oxide. In this case, the layer deposited from the gas phase can be applied directly to the substrate and overcoated with the coating material according to the invention, or vice versa. Particularly favorable are layer combinations in which a layer according to the invention is applied via a layer deposited from the gas phase or lies between two such layers. Substrates coated with the above-mentioned combinations again show improved barrier values, even with a relatively thin hybrid polymer layer (in particular below 10 µm, e. g. in the range of 1 to 5 µm). The substrates coated with a combination of a $SiO_x$ layer and a layer according to the invention showed barrier values with respect to the passage of oxygen and water vapor, which were far below the values required for food packaging.

The lacquers described above can be applied to the drug cores or food. The application can be made by a variety of application techniques (for example, by spraying). Thus, barrier coatings for the tablets or food are obtained after the organic crosslinking of the lacquer.

The application amount is preferably between 3 and 10% by mass. The layer thickness can preferably be adjusted to ranges between 1 to 250 µm, more preferably to 5 to 100 µm.

In addition, the incorporation of inert fillers in the coating is known from the prior art. These should not be chemically reactive, non-hygroscopic, dispersible and have a particle size that does not affect the visual appearance of the coating. Typical fillers are starch, chemically modified starch, dextrin, microcrystalline cellulose, insoluble cellulose derivatives, and inorganic compounds (e.g. talcum, $TiO_2$, $SiO_2$, silicates, clay materials, insoluble carbonates and phosphates). The proportion of the filler (preferably in an amount of 1-25% of the coating) depends on the material. Starch or dextrin improve the mechanical properties and facilitate processability. Inorganic fillers such as silicates improve the moisture barrier. According to the invention, it is found that the silicic acid (hetero) polycondensates with incorporated PCL-T have good adhesion to various substrates and are transparent and biodegradable.

Other features which are considered as characteristic for the invention are set forth in the appended claims.

Materials used: Epoxy-functionalized alkoxysilane (GLYMO), two more metal alcoholates (aluminum tri-sec. butoxide, AsB and a tetraalkoxysilane, usually tetramethoxysilane), ammonium chloride, ammonium hydroxide, ethanol, complexing agent (ethylacetoacetate, EAA), isocyanate-containing alkoxysilane (isocyanatopropyltriethoxysilane), polycaprolactone-triol, hydrochloric acid 0, 1 M.

A1—Functionalization of Polycaprolatonetriol with Triethoxysilane Groups

The functionalization of polycaprolactone-triol (PCL-T) with triethoxysilane groups was based on Liu et al. LIU, P.; HE, L; SONG, J.; Liang, X.; DING, H.: Microstructure and thermal properties of silyl-terminated polycaprolactone-polysiloxanes modified epoxy resin composites. In: Journal of Applied Polymer Science 109 (2008), p. 1 105-1 1 13). First, 50.0 g (166.67 mmol) of PCL-T were dried to remove absorbed water. The drying was carried out under vacuum (rotary vane pump) at 100° C. The functionalization of one-third (or, in the alternative, two-thirds) of the hydroxy groups of the PCL-T was then carried out at 80° C. under argon by adding 41.23 g and 166.67 mmol (42.46 g or 333.34 mmol, respectively) of isocyanatopropyltriethoxysilane to PCL-T dropwise within one hour. The reaction mixture was stirred for 18 h at 80° C. under argon. The reaction was checked for completeness by IR transmission spectroscopy. A broad band between 3750 and 3000 $cm^{-1}$ attributable to the vibrations of the hydroxy groups of the PCL-T is retained, indicating that hydrolysis of the triethoxysilane groups does not take place during the functionalization of the PCL-T. A dominant band of the NCO group at 2272 $cm^{-1}$ had completely disappeared after 18 hours, confirming that all Isocyanato groups of isocyanatopropyltriethoxysilane had been reacted to form a carbamate group. A clear, highly viscous liquid was obtained. The product was characterized by IR transmission (Nicolet 6700, Thermo Fisher Scientific, resolution: 4 $cm^{-1}$, measuring range: 4000 $cm^{-1}$ to 400 $cm^{-1}$) and NMR spectroscopy (DPX400, Bruker). By calculating the integrals in the $^1H$ NMR spectrum, it could be shown that the single functionalization led to 100% of the singly functionalized product and the twofold functionalization gave an almost equally high yield.

A2—Functionalization of Cellulose with Epichlorohydrin and Subsequent Crosslinking with an Epoxy Group-Containing Silicic Acid (Hetero) Polycondensate For functionalization, according to Dong et al [Dong, S.; Roman, M.; J. Am. Chem. Soc. 129 (2007), 13810], 4.00 g (24.66 mmol) of cellulose were dispersed in 328 ml of a 1 M sodium hydroxide solution and then stirred with 2.28 g (24.7 mmol) of epichlorohydrin at 60° C. for 2 h. The resulting white, chalky powder was filtered off and washed with distilled water to neutrality. It was dried at 60° C. and finely minced.

Subsequently, an epoxy group-containing silicic acid polycondensate prepared by the prior art was mixed with the functionalized cellulose; the mixture was subjected to a polymerization reaction.

B—Production and Characterization of Lacquer Systems

| Example | Mass content of the functionalized PCL-T (mass %) | Change in the composition of the lacquer in comparison to the reference lacquer |
| --- | --- | --- |
| 1-PCL-T-1/3 | 16 | Reference lacquer |
| 2-PCL-T-1/3 | 29 | Increase of the content of PCL-T in the lacquer at the expense of GLYMO |
| 3-PCL-T-1/3 | 41 | Increase of the content of PCL-T in the lacquer at the expense of GLYMO |
| 1-PCL-T-2/3 | 16 | Increase of the degree of functionalization of PCL-T |
| 1-PCL-T-1/3 GLYMO | 16 | Increase of the content of GLYMO in the lacquer at the expense of TMOS |
| 1-PCL-T-1/3 TMOS | 16 | increase of the content of TMOS in the lacquer at the expense of GLYMO |

Comparative Example

A standard varnish was prepared using the following components: GLYMO, preferably in an amount of 40-80 mol %, based on all silicon-containing starting materials; TMOS, preferably in an amount of 20-60 mol %, based on all silicon-containing starting materials; aluminum tert-butylate complexed with ethyl acetoacetate, preferably in an amount of 1 and 30 mol %, based on the molar amount of GLYMO plus TMOS.

The complexation of the aluminum tert-butylate serves to slow the hydrolysis and condensation of the aluminum compound to prevent a rapid growth of the oxide network.

For the synthesis of the standard lacquer, AsB was provided and EAA was added dropwise. After the mixture was stirred for 30 minutes, TMOS, GLYMO was added to the batch and mixed homogeneously. Subsequently, water was added dropwise (stoichiometry of 1 to the hydrolyzable groups) and the lacquer mixture was stirred at room temperature for 3 h. A clear colorless sol having a solids content of 49% by weight was obtained.

Example "Reference Lacquer" (1-PCL-T-1/3)

The comparative example was repeated with the proviso that part of the GLYMO was replaced by Si-functionalized PCL-T (one-third of the hydroxy groups replaced) such that the mass fraction of the functionalized PCL-T (based on solids) was 16% by weight.

All other coating systems were prepared starting from the synthesis described above with changes in the lacquer formulation. All changes made are listed in the table above. No changes were made to the basic approach to the synthesis.

Before the subsequent application of the lacquers, all systems were diluted with an ethanol/water mixture (mass ratio 1:1) to a solids content of 22 wt.-% (excluding the antibacterial additive). The completeness of the hydrolysis reaction after the lacquer synthesis was examined by means of Raman spectroscopy (spectrometer RFS 100 from Bruker, power: 500 mW, measuring range: 4000 $cm^{-1}$ to 200 $cm^{-1}$, resolution: 4 $cm^{-1}$).

The durability of the lacquer systems was tested both by Raman spectroscopy and by determination of the kinematic viscosity (Ubbelohdeviskosimeter type AVS 410 of Schott/SI Analytics GmbH).

The determination of the solids content of the lacquer systems was carried out by baking at 200° C. for one hour. In each case a double determination was carried out.

Knife Coating and Curing

The coating of the lacquers was carried out by Erichsen Spiral Squeegee (Model 358) and Coatmaster 509 MC film applicator from Erichsen. It was worked with a spiral squeegee with a film width of 220 mm and a wire winding of 20 µm. The resulting wet film thicknesses were thus in the range of 20 µm. The application speed was 12.5 mm/s. The substrate was PLA film (30 µm) or Cellophane film (45 µm, 20×27 cm) and, for the solid-state NMR samples, a Teflon plate. A PET film (100 µm) was used for the measurements of biodegradation. When checking the layer adhesion, the substrates were pretreated with corona. The curing of the coatings took place at 100° C. for 1 h (PLA films) or 130° C. for 1 h (PET films and Teflon plate) in a convection oven U 80 from Memmert GmbH+Co. KG. After curing, a thickness of the coating of about 5 µm was measured.

Comparably thick coatings can be achieved with conventional methods for tablet coatings.

Assessment of Appearance and Adhesion

The resulting coatings were examined for their appearance and their adhesion to polylactate (PLA) and polyethylene terephthalate (PET) films. The visual appearance was evaluated with the naked eye. The adhesion was determined by means of a tape test, which is derived from the cross-cut technique with adhesive tear (DIN EN ISO 2409). The adhesion of the layer to the substrate is evaluated using the categories TT 0 (the layer is not detached from the substrate by the test) to TT 5 (the layer is completely detached from the substrate). For the test, an adhesive tape with a defined bond strength was glued bubble-free on the coating and pressed. After a period of 1 min, the adhesive tape was peeled off within one second at an angle of about 60° to the pulling direction and then the adhesion was evaluated.

With all materials, a transparent, smooth, homogeneous, defect-free coating was obtained. Regardless of the selected PCL-T content and the other variations of the lacquer composition, all layers had the same, good, quality. The tape test gave the following values:

|  | PLA | | PET | |
| --- | --- | --- | --- | --- |
| bioORMOCER® | without corona | with corona | without corona | with corona |
| 1-PCL-T-1/3 | TT5 | TT0 | TT1 | TT0 |
| 2-PCL-T-1/3 | TT5 | TT1 | TT1 | TT0 |
| 3-PCL-T-1/3 | TT5 | TT2 | TT2 | TT0 |
| 1-PCL-T-1/3-TMOS | TT5 | TT1 | TT1 | TT0 |
| 1-PCL-T-1/3-GLYMO | TT5 | TT0 | TT0 | TT0 |
| 1-PCL-T-2/3 | TT5 | TT0 | TT0 | TT0 |

Biodegradability

The biodegradability of the coatings produced was tested according to standard ISO 14885-1:2005 and by storage of the samples in a compost. The coated PET films were clamped in a slide frame for the compost test and connected at the back with a non-degradable control sample (coating on PET film). The samples were then placed vertically in the compost so that the entire sample was covered by soil. The compost was made from so-called dry active compost of Kompostwerke Würzburg GmbH, water (approx. 50% by weight, based on the dry compost) and Radivit® compost accelerator from Neudorff (about 5 g per liter of compost). The microorganisms of the compost and the compost accelerator are active for about two to three weeks. The compost was changed every 3 weeks and all samples were carefully cleaned and photographed. With visible signs of biodegradation, the samples were examined by laser scanning microscopy (VK-X200 from Keyence Corporation).

The storage of the coatings of 1-PCL-T-1/3, 2-PCL-T-1/3 and 3-PCL-T-1/3 in the compost led to first degradation phenomena that were the stronger the higher the PCL-T content was in the material. Biodegradability with the help of compost microorganisms is an indicator that the layer materials are decomposed also by higher organisms, including mammals and humans, or by their intestinal bacteria.

Forming of Networks

The inorganic network density of the cured coating systems was investigated by $^{29}Si$ solid-state HPDEC/MAS NMR spectroscopy. By assigning the T and Q groups, it was possible to ensure that all participating precursors were integrated into the inorganic network.

The inorganic network density could be estimated from the intensity ratios of the T groups. Table 1 shows the network density of the different lacquer systems in comparison.

TABLE 1

| Density of the inorganic network of < | Density of the inorganic network of < | Density of the inorganic network of |
| --- | --- | --- |
| 2-PCL-T-1/3 | 1-PCL-T-1/3 | 1-PCL-T-1/3-GLYMO |
| 1-PCL-T-1/3-TMOS | | 1-PCL-T-2/3 |

In Table 2 below, the crosslink density of the organic and inorganic network structure of the cured layer systems is classified based on the evaluation of the $^{13}C$ solid-state NMR and $^{29}$Si solid-state NMR spectra in relation to the reference system 1-PCL-T-1/3.

TABLE 2

| Lacquer system | Comparison of the density of the crosslinking of the inorganic network | Comparison of the density of the crosslinking of the organic network |
|---|---|---|
| 2-PCL-T-1/3 | more open | slightly higher density |
| 1-PCL-T-1/3 TMOS | more open | 0 |
| 1-PCL-T-1/3 (reference system) | 0 | 0 |
| 1-PCL-T-1/3 | higher density | 0 |
| 1-PCL-T-2/3 | higher density | slightly more open |

Barrier Properties

SiO$_x$ layers on polyethylene terephthalate (PET/SiO$_x$) applied by means of PVD (Physical Vapor Deposition) have water vapor permeabilities (WVTR) in the range of 0.12 g/m$^2$/d. Their oxygen permeabilities (OTR) are about 0.23 cm$^3$/m$^2$/d/bar. These values are slightly above the values required for food packaging of 0.10 g/m$^2$/d for the WVTR and of 0.1 cm cm$^3$/m$^2$/d/bar for the OTR. In case this inorganic layer is combined with a "classic" hybrid layer of organically modified silicic acid (hetero) polycondensates such as the "standard lacquer" described above, these values can be decreased by up to 92% (WVTR) or 96% (OTR) at layer thicknesses of about 1 to 5 μm and can thus be decreased to values required for food packaging. For a combination of a SiO$_x$ layer with one of the layers according to the invention, at comparable layer thicknesses values could be determined which are still reduced by 69-85% (WVTR) or 87-91% (OTR) compared to the PET/SiO$_2$ system. This shows that the incorporation of biodegradable components into the silicic acid (hetero) polycondensate only slightly decreases the layers' excellent barrier properties. The low water vapor transmission rate is particularly astonishing.

Accordingly, the coatings according to the invention are suitable for the production of coating materials for food and pharmaceutical products.

DESCRIPTION OF THE INVENTION

Figure 1:
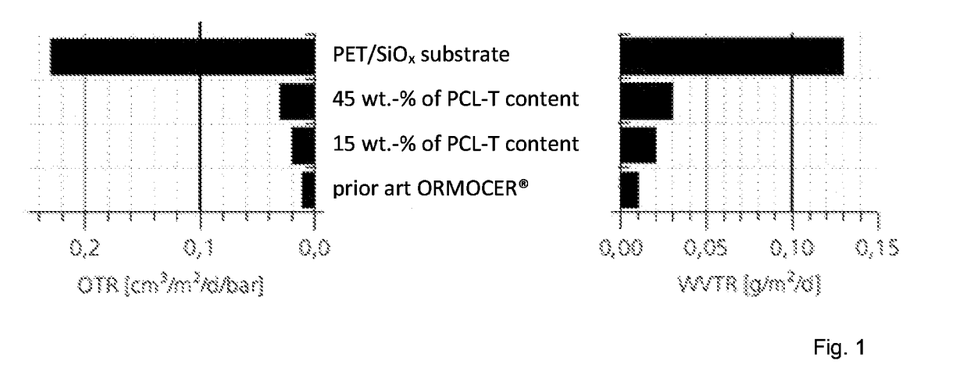
FIG. 1 includes two diagrams showing determined values.

The attached FIG. 1 shows the determined values. The "prior art ORMOCER®" herein means a lacquer made of a hybrid material according to the above-described comparative example. The coating referred to as "45% by weight of PCL-T content" is approximately equivalent to Example 3-PCL-T-1/3 above, except that a slightly larger proportion of GLYMO was replaced with PCL-T such that the content of PCL-T was increased from 41 to 45 wt.-%. The coating referred to as "15% by weight of PCL-T" corresponds approximately to Example 1 above -PCL-T-1/3, i. e. the reference lacquer, but with slightly less GLYMO replaced with PCL-T so that its content is only 15% by weight.

A flawless look is necessary for use as a tablet or food coating. The optics of two developed coatings on a polyethylene terephthalate-based (PET) substrate were investigated. The developed biopolymer-containing layers had either 30% by weight of chitosan or 45% by weight of PCL-T on a PET substrate. In both produced PCL-T or chitosan-containing coatings, a transparent, smooth, homogeneous surface was obtained which showed no defects. Regardless of the chosen biopolymer content, the layers exhibited the same good optical quality with excellent adhesion to the substrate.

Biodegradable Layers with Good Barrier Properties

Tablet coatings, in particular, require extremely good barrier properties against odors, water vapor and oxygen, when oxygen or water-vapor-sensitive agents are involved. By matching the network density and polarity of the hybrid polymeric coating material, it is possible in combination with inorganic oxide layers, such as SiO$_x$ (1.5<x<1.8) to achieve very good barrier values [Amberg-Schwab, S.: Handbook of Sol-Gel Science and Technology, Vol. 3, Ed.: S. Sakka, Kluwer Academic Publishers, Norwell, Chap. 21 (2004), p. 455]. The applied hybrid polymer layer reduces micro- and nanoporosity.

The combination with an inorganic oxide layer may constitute a functional coating. The material used according to the invention can be present in a layer composite with one or more other, preferably inorganic, layers. The layer composite is edible.

Exemplary of the invention, the oxygen permeability and the water vapor permeability, each with and without hybrid polymer barrier coating, were examined. The investigation of the oxygen permeability was carried out according to DIN 53 380 (23° C., 50% rh, relative humidity), the investigation of the water vapor permeability was carried out according to DIN 53 122 (23° C., 85% rh, relative humidity). The substrate showed an oxygen permeability of 160 cm$^3$/m$^2$×d×bar, for the substrate coated with hybrid polymer an oxygen permeability of 10 cm$^3$/m$^2$×d×bar. For the water vapor permeability, the biodegradable model substrate had a value of 140 g/m$^2$×d, and for the hybrid polymer-coated biodegradable model substrate a value of 30 g/m$^2$×d.

FIG. 1 shows the oxygen (OTR, at 50% RH and 23° C.) and water vapor transmission rate (WVTR, at 90% RH and 38° C.) of the developed chitosan and PCL-T containing coatings in a layer system of PET film and SiO$_x$ layer. The mark at 0.10 cm$^3$/m$^2$×d×bar at the oxygen permeability and the mark at 0.10 g/m$^2$×d at the water vapor permeability represent the barrier requirement for food packaging.

Cytotoxicity Studies

Figure 2:
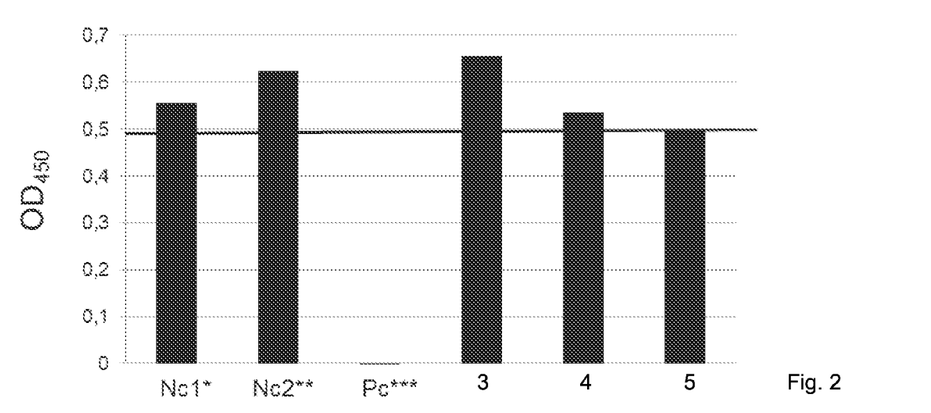
FIGS. 2 and 3 are diagrams showing the in vitro cytotoxicity of some PCL-T materials.
Figure 3:
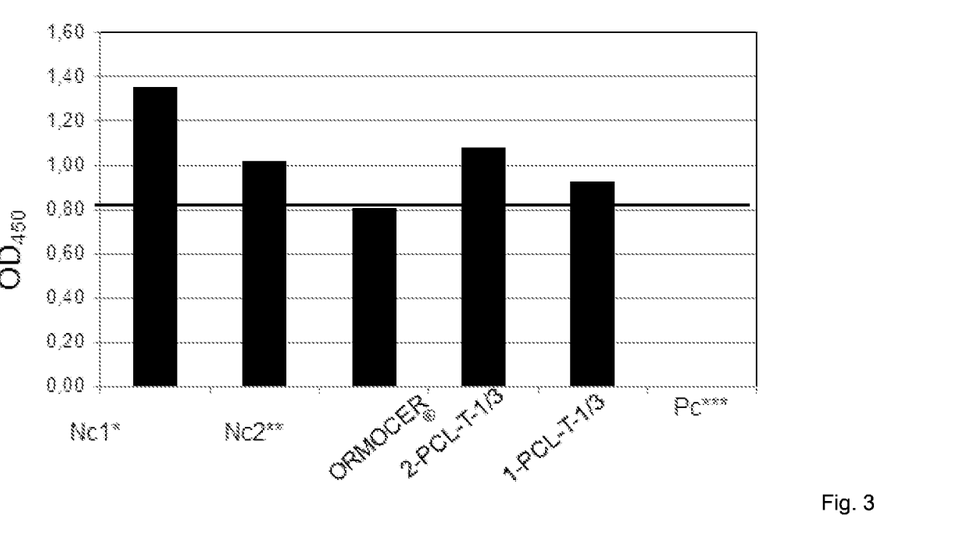

FIGS. 2 and 3 show the in vitro cytotoxicity of some PCL-T materials.

FIG. 2: In vitro cytotoxicity of glass slides coated with the lacquer usable according to the invention.

Cells of the murine fibroblast cell line (L929) grew for 24 h on three glass plates coated with various organically modified silicic acid polycondensates. After the tetrazolium-containing reagent WST-1 was added, the optical density (OD$_{450}$) of the cell culture was measured. 3 shows the result for the glass plate with reference varnish, 4 shows the result for the glass plate with 2-PCL-T-1/3, and 3 shows the result for the glass plate with 1-PCL-T-1/3.

In the figure:
a)=cells were grown on well bottoms (in the vessel, without glass substrate)

b) *=cells were grown on the glass plates

***=cells were grown on well bottoms and treated toxically with 1% SDS (i. e. targeted killed to mimic a toxic substrate) (SDS=sodium dodecyl sulfate)

Since the L929 viability is proportional to the value of the optical density of the cell culture, the cytotoxicity can be determined from $OD_{450}$: A sample is considered non-cytotoxic if $OD_{450}$ is ≥80% of the blank Nc2 value (the black line indicates this area).

FIG. 3: In vitro cytotoxicity of glass slides coated with the lacquer which can be used according to the invention.

Silicic acid polycondensate extracts were obtained by shaking the sterile with the silicic acid polycondensate coated glass plates for 24 h in a cell culture medium (DMEM—Dulbecco's Modified Eagle Medium) under physiological and aseptic conditions. Subsequently, the sub-confluent cell cultures (L929) were incubated in undiluted extraction solutions for 24 h and prepared analogously to the previous film to determine $OD_{450}$. "Ormocer" refers to the reference lacquer.

In the figure:
a)=cells were grown on well bottoms (in the jar, without glass substrate)

**=cells were grown in the medium, which was incubated like the extracts for 24 hours b) *>=cells were grown on well bottoms and toxically treated with 1% SDS (i. e. targeted killed to mimic a toxic substrate) (SDS=sodium dodecyl sulfate)

The figures show that the two coating materials which can be used according to the invention are not cytotoxic to mammalian cells since they reach the minimum value. Therefore, these compositions can be used as coatings for medicines and foods.

Extract from contact with organically modified silicic acid polycondensate without biodegradable groups is weakly cytotoxic. Due to a biodegradable, harmless coating on the tablets, which have excellent barrier properties, it is possible to replace PVDC and aluminum with alternative packaging materials that do not have any outstanding barrier effect, but are deep-drawable. In addition, alternative, simpler packaging concepts are conceivable, for example, a waiver of the separation in blister packs.

The properties of the highly functional coating materials can be adjusted, combined and customized in addition to the barrier effects. As explained above, the coatings are, for example, stable in an acidic environment, but can also be adjusted so that they dissolve already in the stomach. The composition of the coating can be chosen so that it behaves harmlessly in the body.

Due to the excellent barrier properties of the newly developed coating, it will be possible to save on the packaging materials chlorine-containing films and aluminum foils in future. Alternative, cheaper packaging concepts are conceivable. The barrier coating also improves the shelf life of pharmaceutical products and food. In addition, the use according to the invention makes it possible to produce products which are edible coatings and have the following properties:

No toxic, allergenic and non-digestible substances
Prevent structural stability and mechanical damage during transport, handling and sales
Good adhesion to the food surface and uniform coating
Semipermeable: For some products a controlled gas or water migration into and out of the product to be protected is desirable. Examples are the fruit and vegetable transport, as the products are often subject to a maturing process during transport to the trade (aerobic and anaerobic respiration).
Preventing the uptake or release of components which stabilize the flavor, the taste, nutrients and organoleptic properties; without changing the taste or the visual appearance
Ensuring biochemical and microbial stability while protecting against contamination, pest infestation, microbial proliferation and other types of disintegration
Maintaining or improving the aesthetic and sensory attributes (appearance, taste, etc.) of the food
Use as a carrier for desired additives such as: taste, smell, color, nutrients and vitamins. Incorporation of antioxidants and antimicrobial agents.
Simple and inexpensive production

The invention claimed is:

1. A method for preparation of a coated edible product selected from the group consisting of coated medicines and coated foods, which comprises the steps of: (i) applying a coating composition, which contains an organo-modified silicic acid polycondensate, to a drug or food substrate; and (ii) drying and/or curing the coating composition.

2. The method according to claim 1, which comprises prior to the step (i) or after the step (ii) an additional step (iii) in which the drug or food substrate is at least partially coated with a metal oxide layer.

3. The method according to claim 1, wherein the coating composition contains silicic acid polycondensate modified with organic groups.

4. The method according to claim 1, wherein the coating composition is present in a diluent and/or solvent.

* * * * *